United States Patent [19]

McLees

[11] Patent Number: 5,059,180
[45] Date of Patent: Oct. 22, 1991

[54] AUTOMATIC NEEDLE TIP GUARD

[76] Inventor: Donald J. McLees, 2623 Virginia Ave., Everett, Wash. 98201

[21] Appl. No.: 439,417
[22] Filed: Nov. 21, 1989
[51] Int. Cl.⁵ ............................................. A61M 5/00
[52] U.S. Cl. .................................. 604/110; 604/198; 604/263
[58] Field of Search ................ 604/110, 192, 197–198, 604/263

[56] References Cited

U.S. PATENT DOCUMENTS

| | | | |
|---|---|---|---|
| 4,804,371 | 2/1989 | Vaillancourt | 604/198 |
| 4,887,998 | 12/1989 | Martin et al. | 604/110 |
| 4,894,055 | 1/1990 | Sudnak | 604/198 |
| 4,911,693 | 3/1990 | Paris | 604/192 |
| 4,921,490 | 5/1990 | Spier et al. | 604/192 |
| 4,946,446 | 8/1990 | Vadher | 604/198 |
| 4,966,593 | 10/1990 | Lennox | 604/198 |

Primary Examiner—C. Fred Rosenbaum
Assistant Examiner—Corrine Maglione

[57] ABSTRACT

A guard for the tip of a hypodermic needle which is activated automatically when the needle is withdrawn after use. The guard resides initially around the shaft of the needle near the needle tip. Insertion of the needle causes the guard to be pushed back by the surface of the skin. This releases the spring activated locking mechanism such that when the needle is withdrawn the spring pushes the guard over the tip of the needle and the guard becomes automatically locked in place.

1 Claim, 4 Drawing Sheets

AUTOMATIC NEEDLE TIP GUARD

BACKGROUND OF THE INVENTION

To prevent health care workers who handle used hypodermic needles from contracting AIDS or hepatitis or the like through an accidental needle prick, it would be desirable to have incorporated into the design of single use needles a guard which would automatically enclose the needle tip when the needle is withdrawn. Thus health care workers would be protected as would anyone else who might accidentally come in contact with a contaminated needle before it has been properly disposed of or recycled. This would include medical personnel who must draw blood in order to determine the presence of infectious disease. Also it would be more difficult for drug abusers to reuse a single use needle equipped with such a guard.

Obviously it would be important that such a guard not interfere with the operation of the needle to a significant extent and be as simple and low cost as possible yet still work entirely automatically such that no further action beyond insertion of the needle and withdrawal be required of the operator. If activation of the guard were on an elective basis, in many cases it would simply not be used. Also, manual activation complicates usage and requires further manipulation which itself could be dangerous. The guard must also be fail safe so that the needle cannot puncture the guard even when very high pressure is applied.

The prior art reveals a great variety of needle guards, but all fall short of achieving the objects of this present invention. Many early guards (1960's and 1970's) themselves created a danger by requiring the operator to manually force the guard in such a manner that accidental puncture could result. Also many were not fail safe. Pressure on the end of the needle guard could cause penetration by the needle tip.

More recently issued patents show technology which alleviates many of the problems, but still does not satisfy all the objectives of this invention. The Self-capping Needle Assembly of Dombrowki and Welch, U.S. Pat. No. 4,790,828 (1988), shows tip guards which do not require motion toward the sharp tip to activate (thus reducing danger to the operator) and have one way gates entrapping the tip once the guard is in place. However, they do require the operator to supply the force for positioning the guard after needle use and the guards occupy a substantial portion of the needle shaft in their initial position, possibly dictating the use of a longer needle than normal. One version is not fail safe because the guard can be easily pulled off the end of the needle. In all versions the sharp tip can come in contact with and possibly puncture the end of the guard unless the guard is fabricated from a substantially stout material, which would increase cost and detract from feasibility.

Vaillancourt shows an embodiment of his Post-injection Needle Sheath (U.S. Pat. No. 4,725,267) which eliminates the need for the attendant to supply the physical force necessary to place the guard by employing a compression spring for positioning. However, the guard is not automatic. The attendant must still push or turn a mechanism to initiate operation of the spring. The guard is not completely fail safe because it is possible to position the guard such that the needle could escape. Also, even with the guard positioned to entrap the needle the sharp point can easily come in contact with the end of the cap and perhaps pierce it should it be subjected to a sudden accidental extreme pressure.

SUMMARY OF THE INVENTION

It is an object of this invention to provide a needle tip guard which operates entirely automatically and requires no additional action on the part of the operator beyond the normal process of insertion and withdrawal. It is a further object to provide a needle tip guard which has a mechanism for automatically placing the guard that becomes initiated when the needle penetrates the skin and automatically places the guard over the tip of the needle when the needle is withdrawn. Thus the act of using the needle automatically causes the guard to operate. Another object is to provide a guard mechanism which is irreversible in that once the guard encloses the end of the needle, the needle tip cannot escape. Another object is to provide such a guard which cannot be pulled off the end of the needle. Another object is to provide a guard mechanism which will not allow the needle tip to penetrate the guard even under extreme accidental pressure. Another object is to provide such a guard which, once it is used and therefore encloses the needle tip, cannot be easily defeated by drug abusers. A still further object of the invention is to provide such a guard mechanism which is as simple as possible in order to minimize production costs and as small as possible to allow most of the length of the needle to be useable and at the same time minimize material cost.

All of the objectives of the invention can be achieved with a simple three part mechanism consisting of a spring, a ball, and a hollow "bead" or guard housing. The mechanism is used in conjunction with a needle that has a raised rounded shoulder near the distal end (or tip). The shoulder need only be a few thousandths of an inch high and would not interfere with the normal entry and withdrawal of the needle. The hollow bead is flattened on one side so as not to limit the angle at which the needle enters and is free to rotate on the needle shaft so as to not restrict the rotational position of the needle. The spring is very small and weak so as to not require any noticeable increase in needle insertion force for compression. It need only have enough force to hold the guard against the needle shoulder in the initial position and then push the very small ball and bead over the needle tip at withdrawal. The bead can be of any suitable material although plastic would probably be the least costly in terms of fabrication expense. The ball can be of any suitable material also, but a hard plastic would be sufficient, light in weight, and probably the most cost effective material. The ball serves multiple functions. In the initial position it is a critical part of the lock mechanism, preventing the bead from moving past the needle shoulder. As the needle penetrates the surface of the skin and the bead is moved up the needle shaft, the ball becomes an actuator by releasing its hold against the shoulder. After withdrawal and the ball and bead have been pushed over the tip of the needle by the spring, the ball becomes the bead end hole closure and tip protector, preventing the sharp needle tip from contacting and possibly rupturing the bead material. The mechanism of operation and verification that the mechanism satisfies the objectives of the invention will be more apparent after reference to the drawings.

DETAILED DESCRIPTION OF THE DRAWINGS

Figure 1:
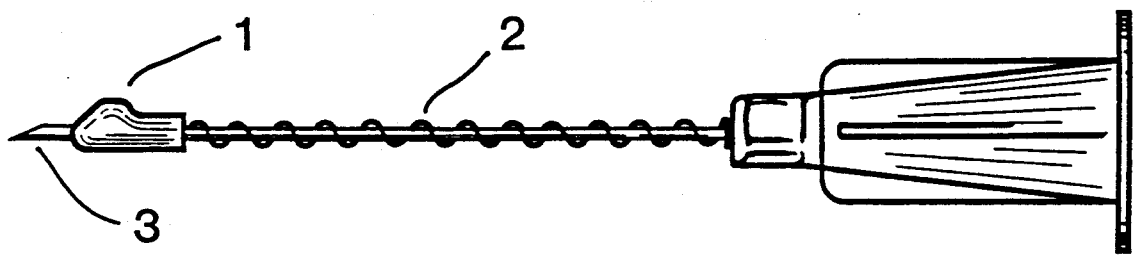
FIG. 1 is a side view of a typical hypodermic needle with the automatic needle guard in place near the needle tip.

The guard bead 1 and spring 2 can be seen in FIG. 1. Here the guard is shown in its initial position near the sharp end of a typical hypodermic needle, although the needle is different from the standard type in that a relatively short portion 3 near the tip is larger in diameter than the rest of the needle shaft.

Figure 2:
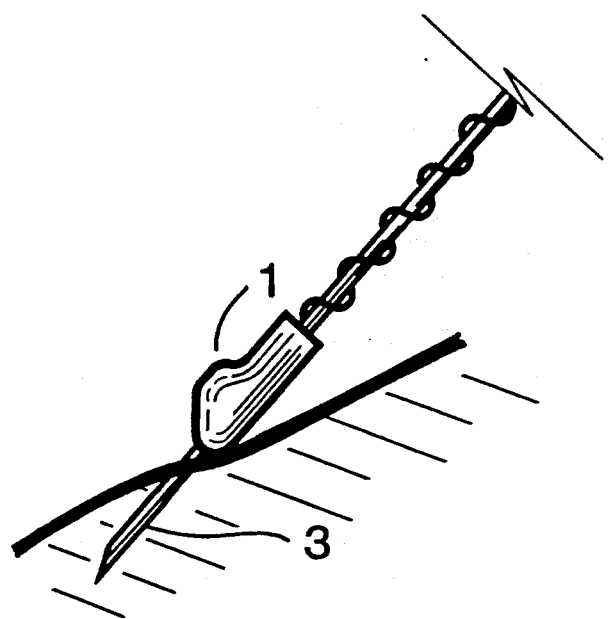
FIG. 2 is an enlarged side view of the needle tip penetrating the skin, which is shown in side view cross section.

In FIG. 2 the enlarged tip portion 3 can be seen after completely penetrating the surface of the skin, which appears in cross section. As the needle penetrates further, the guard 1 is pushed further up the needle shaft against the very weak spring force by the skin surface. The penetration distance would be limited only by the length the spring would require on the needle shaft when completely compressed. The initial position of the guard leaves enough of the tip exposed to allow entry at even a very shallow angle.

FIG. 3 is a series of drawings illustrating how the guard mechanism works. In this sequence center sections only are used to show the guard bead 1 and individual spring coils 2 so as to avoid unnecessary cluttering and thereby better illustrate the principle of operation.

Figure 3A:
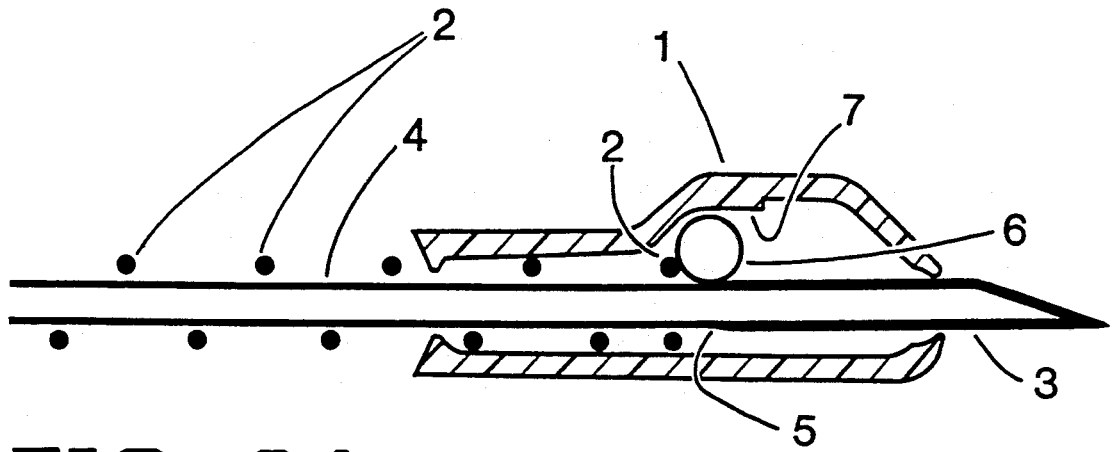
FIGS. 3A through 3G are side view cut away diagrams showing the operating sequence of the mechanism. The needle and ball can be seen inside the bead. Longitudinal center sections only are shown for the bead and the individual spring coils.

In FIG. 3A the enlarged tip portion 3 of the needle 4 can be seen. The two diameters meet at a tapered shoulder 5 which can be as small as a few thousandths of an inch depending on the particular specific needle gauge and chosen design parameters. FIG. 3A shows what the initial position configuration looks like inside the guard. The ball 6 is simultaneously in contact with the spring 2, tapered shoulder 5, and roof of the primary chamber 7. The spring is in a partially compressed state and is therefore exerting a force against the ball. However, the inside dimensions of the primary chamber are not large enough to allow the ball to be pushed past the shoulder.

Figure 3B:
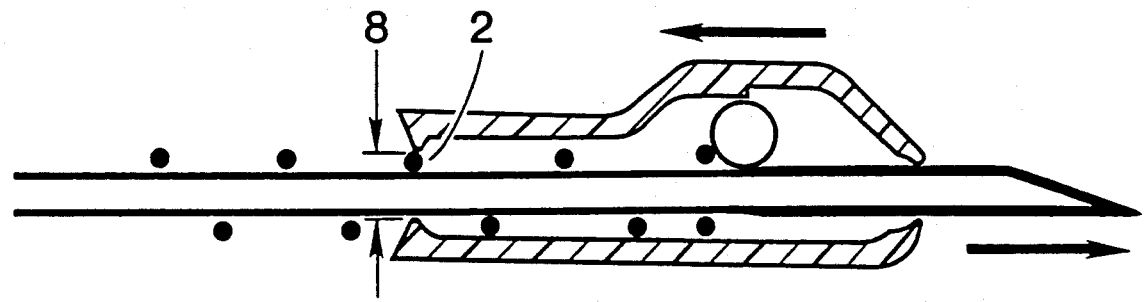

While the ball must remain stationary relative to the needle, the guard is free to be pushed rearward by the surface of the skin or any other outside force as shown in FIG. 3B. In this figure the ball is still trapped in the primary chamber between the needle shoulder and the top of the chamber even though the guard bead has been pushed back substantially. It can be observed here that the round opening 8 at the back of the guard is large enough in diameter to allow the spring to pass through, although in doing so the guard is forced to wobble as the individual spring coils move through the constriction. FIG. 3B shows the guard tilted up at the rear as the top of one spring coil 2 has just reached the center of the rear guard opening.

Figure 3C:
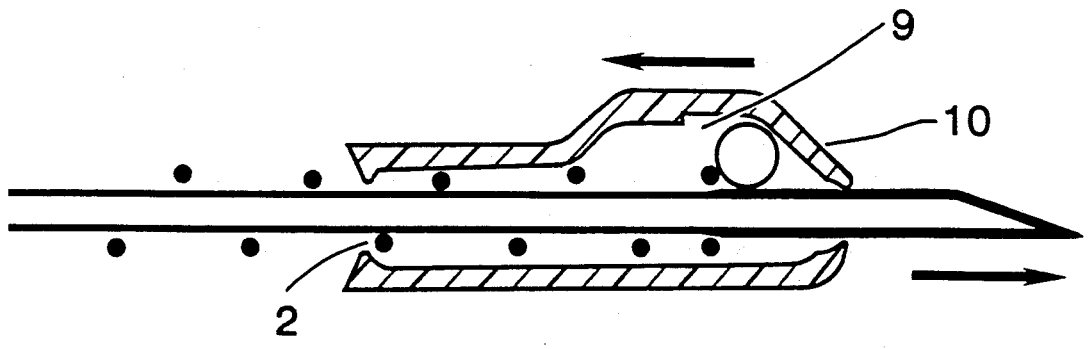

In FIG. 3C the guard is still being pushed back, but now the guard has been moved back far enough so that the ball has entered the guard bead secondary chamber 9. The internal dimensions of the secondary chamber are large enough to allow the spring to push the ball over the needle shoulder and against the forward wall 10 of the guard bead. So in FIGS. 3A and 3B the ball and spring remain in place relative to the needle as the guard is pushed back. But when the secondary chamber reaches the ball, the spring is free to suddenly expand and snap the ball against the front interior wall of the guard as shown in FIG. 3C. The actual forces involved are so weak and the components so small that this action would probably hardly be noticed by the person operating the needle, with the possible exception of a slightly noticeable quick wobble as the spring moves rapidly through the rear opening and as the ball moves toward contacting the forward wall. In this particular position in FIG. 3C the bottom of a spring coil 2 has just passed through the rear opening constriction and the guard has therefore now wobbled to the point where it is tilted back relative to the needle.

Figure 3D:
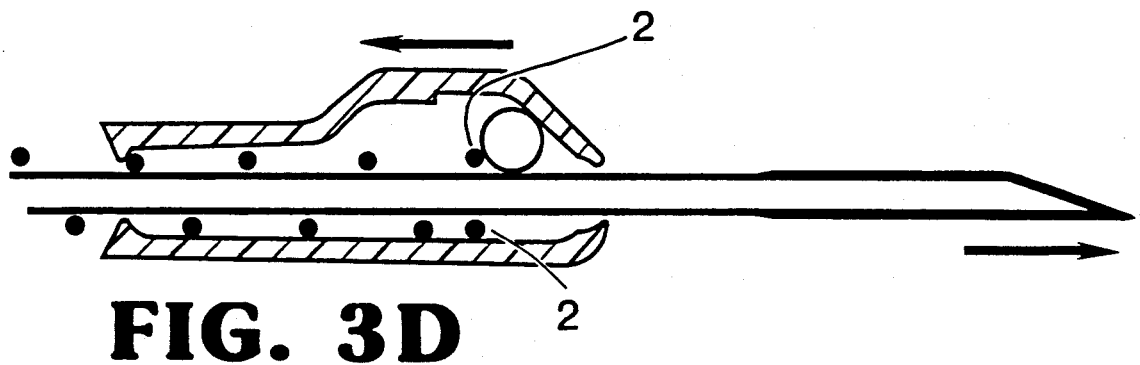

In FIG. 3D the guard, ball, and spring are still being pushed back, and can continue to be pushed back until the individual spring coils are touching. Here it can be seen that the distance between individual spring coils has been reduced due to compression of the spring. It can also be noted that the forward most coil 2 has been wound perpendicular to the spring longitudinal axis so that the spring always intercepts the ball straight on even if the spring should rotate.

Figure 3E:
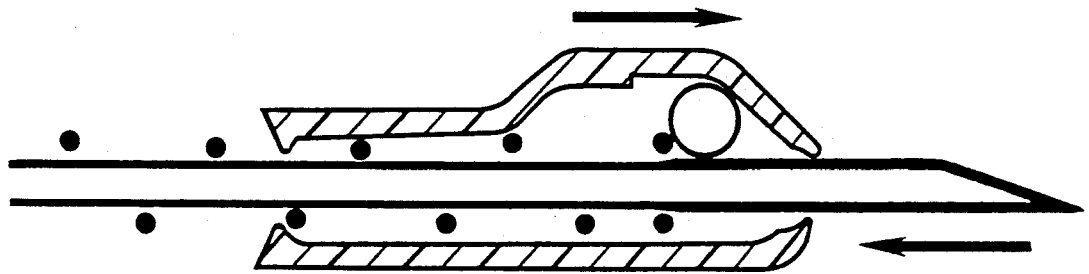

In FIG. 3E the needle is being withdrawn. Spring force acting through the ball keeps the guard against the skin surface. The important difference is that now, since the spring force keeps the ball pushed to a forward position in the larger secondary chamber, the ball moves easily over the needle shoulder and the entire guard assembly can be pushed by the spring over the needle tip.

Figure 3F:
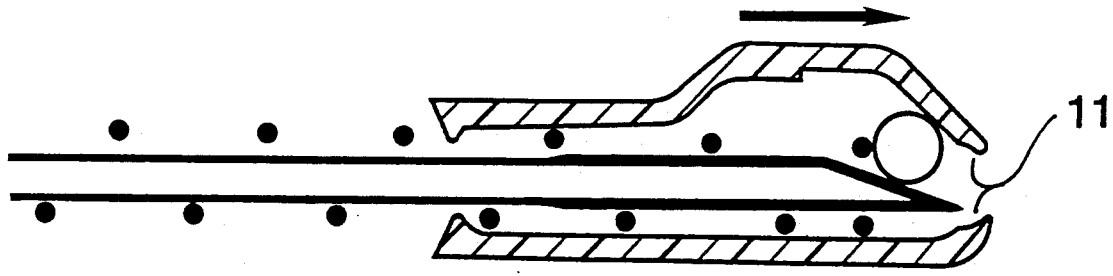

In fact in FIG. 3F the needle has been completely withdrawn and the spring is in the process of pushing the ball and therefore also the front end of the guard bead past the needle tip. The dimensions of the spring and the ball and the internal dimensions of the secondary chamber are such that as the ball is being pushed forward it is forced to follow the incline of the forward wall toward the front ball cavity 11.

Figure 3G:
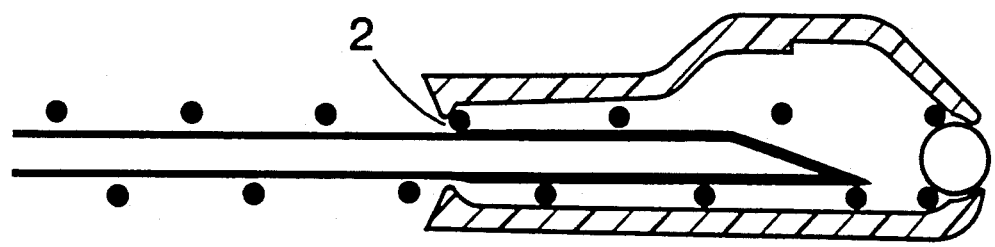

FIG. 3G shows the guard locked into its final position. The spring has pushed the ball completely into the front ball cavity and has also pushed the guard bead to its maximum extension. The outside diameter of the needle tip plus the cross sectional diameter of an individual coil 2 is greater than the rear opening diameter and the guard is therefore wedged against the needle shoulder. So the guard cannot move forward and it can move back only until the needle point contacts the ball, which now is in place blocking the exit of the needle. The tip of the needle is now completely enclosed and locked securely inside a guard of substantial strength. Since the ball's diameter is greater than the wall thickness of the guard bead, the end of the guard would have to rupture before the needle could exit. The guard can be made of such a material and designed such that should the guard be subjected to an extreme outside force, the needle would bend and collapse on itself before it could puncture the guard, thus guaranteeing the safety of health care workers from infection resulting from an accidental prick of a contaminated needle.

Obviously a variety of different designs perhaps incorporating additional or different parts are possible which would also satisfy the objectives of this invention. What is presented here is the simplest form of the preferred embodiment which still clearly defines the essence of the invention. For example it would be possible to offer a design which eliminates the wobble as the guard moves, but to no particular functional advantage. The basic elements of the invention as defined by the claims would remain unchanged.

Hopefully it is obvious that the objectives of the invention have been met. This entirely automatic needle guard uses a bare minimum of material and only one non-standard moving part- the guard bead itself- in conjunction with a shouldered needle and two very common and inexpensive standard parts— a coil spring and a ball- in providing a protective device strong enough to contain the sharpest of needles.

Also, while this mechanism has been created primarily to be used as a needle guard, other applications of the concept are possible. It can be applied to a variety of similar apparati wherein it is desirable to have motion in one direction effect the release of a mechanism which then moves in the opposite direction. An example of this that most people would be familiar with is the release mechanism of an umbrella. The mechanism can replace the conventional umbrella latch. A person could then close the opened umbrella by first moving the latch up slightly and then releasing.

What is claimed is:

1. A hypodermic needle and automatically activated hollow guard for the tip of the needle through which the needle passes comprising:

a hypodermic needle having a pointed distal tip and a standard hub attached to a proximal end, the surface of said needle being raised at a location substantially near the distal needle tip to form a shoulder facing said proximal needle hub; and a ball inside said guard; and a partially compressed coil spring extending from said needle hub to said ball, the coils of said coil spring being concentric to the axis of said needle, said needle tip guard having an inner chamber, defining an inner wall, of two portions, the proximal portion being nearer the needle hub and the distal portion being nearer the needle tip, said proximal portion having a proximal opening larger than the combined radial size of said spring and said needle on the proximal side of said needle shoulder and thereby allowing said spring and said needle to pass therethrough, said guard being held in its initial position by the force of said partially compressed spring wedging said ball proximal portion of said inner chamber, said proximal opening being smaller than the combined radial size of said spring and said needle on the distal side of said spring and said needle on the distal side of said needle shoulder, said distal portion of said inner chamber having a distal opening through which said needle passes, said distal opening being larger than the needle diameter and smaller than the diameter of said ball, said distal portion of said inner chamber having a clearance between the surface of the needle on the distal side of said needle shoulder and the inner wall of said distal chamber portion greater than said ball diameter and thereby allowing movement of said ball to a position on the distal side of said needle tip and occluding said distal opening, said movement of said ball being initiated by movement of said guard away from said needle tip due to insertion of said needle into a patient.

* * * * *